United States Patent [19]
Cerri et al.

[11] Patent Number: 6,166,275
[45] Date of Patent: Dec. 26, 2000

[54] FLUORINATION PROCESS

[76] Inventors: Gustavo Cerri, 3 Pine Tree Pl., Parsippany, N.J. 07054; Maurice William Hunt, 109 W. Mantua Ave., Wenonah, N.J. 08090; David William Keeler, 5 Wilkeshire Blvd., Randolph, N.J. 07869; Frank Peter Young, 77 Cherryville Stanton Rd., Flemington, N.J. 08822

[21] Appl. No.: 09/398,745

[22] Filed: Sep. 17, 1999

Related U.S. Application Data

[63] Continuation-in-part of application No. 08/972,531, Nov. 18, 1997, abandoned.

[51] Int. Cl.$^7$ .................................................... C07C 17/08
[52] U.S. Cl. .................... 570/167; 570/165; 570/166; 570/168; 570/169
[58] Field of Search ...................................... 570/166, 167, 570/168, 169, 165

[56] References Cited

U.S. PATENT DOCUMENTS

| | | | |
|---|---|---|---|
| 2,749,374 | 6/1956 | Ruh et al. | 260/653 |
| 2,749,375 | 6/1956 | Ruh et al. | 260/653 |
| 4,091,043 | 5/1978 | Ohsaka et al. | 260/653.7 |
| 5,347,059 | 9/1994 | Pennetreau et al. | 570/166 |
| 5,495,057 | 2/1996 | Kyung et al. | 570/167 |

FOREIGN PATENT DOCUMENTS

| | | | |
|---|---|---|---|
| 19133/97 | 11/1997 | Australia . | |
| 95/35271 | 12/1995 | WIPO | 570/166 |
| WO95/35271 | 12/1995 | WIPO . | |
| WO 97/11043 | 3/1997 | WIPO . | |

Primary Examiner—Alan Siegel
Attorney, Agent, or Firm—Colleen D. Szuch; Marie L. Collazo

[57] ABSTRACT

A liquid phase fluorination process for producing difluoromethane without corrosion is provided. In the process of this invention, methylene chloride and hydrogen fluoride are reacted in a reactor made of fluorinated polymer to produce a reaction product while a vaporized and superheated recycle stream of process reactants is fed into the reactor.

7 Claims, 3 Drawing Sheets

FLUORINATION PROCESS

This application is a CIP of Ser. No. 08/972,531 filed Nov. 18, 1997 now abandoned.

FIELD OF THE INVENTION

The present invention relates to a hydrofluorination process. In particular, this invention provides a liquid phase hydrofluorination process for producing difluoromethane that exhibits efficient heat transfer and high productivity and that eliminates corrosion in the reactor system.

BACKGROUND OF THE INVENTION

Liquid phase fluorination processes using antimony pentachloride catalysts to produce chlorofluorocarbons ("CFC's") and hydrochlorofluorocarbons ("HCFC's") are well known. CFC's and HCFC's have been implicated in the depletion of the earth's ozone layer and, thus, a need has developed for processes for the production of hydrofluorocarbons ("HFC's"), which are believed not to deplete the ozone layer. One HFC of particular interest is difluoromethane ("HFC-32"). Known liquid phase processes for producing HFC-32 using antimony pentachloride catalysts are very corrosive of the materials of construction used in the process. Therefore, a need exists for a liquid phase fluorination process for producing a HFC's that overcomes this problem.

DESCRIPTION OF THE INVENTION AND THE PREFERRED EMBODIMENTS

Figure 1:
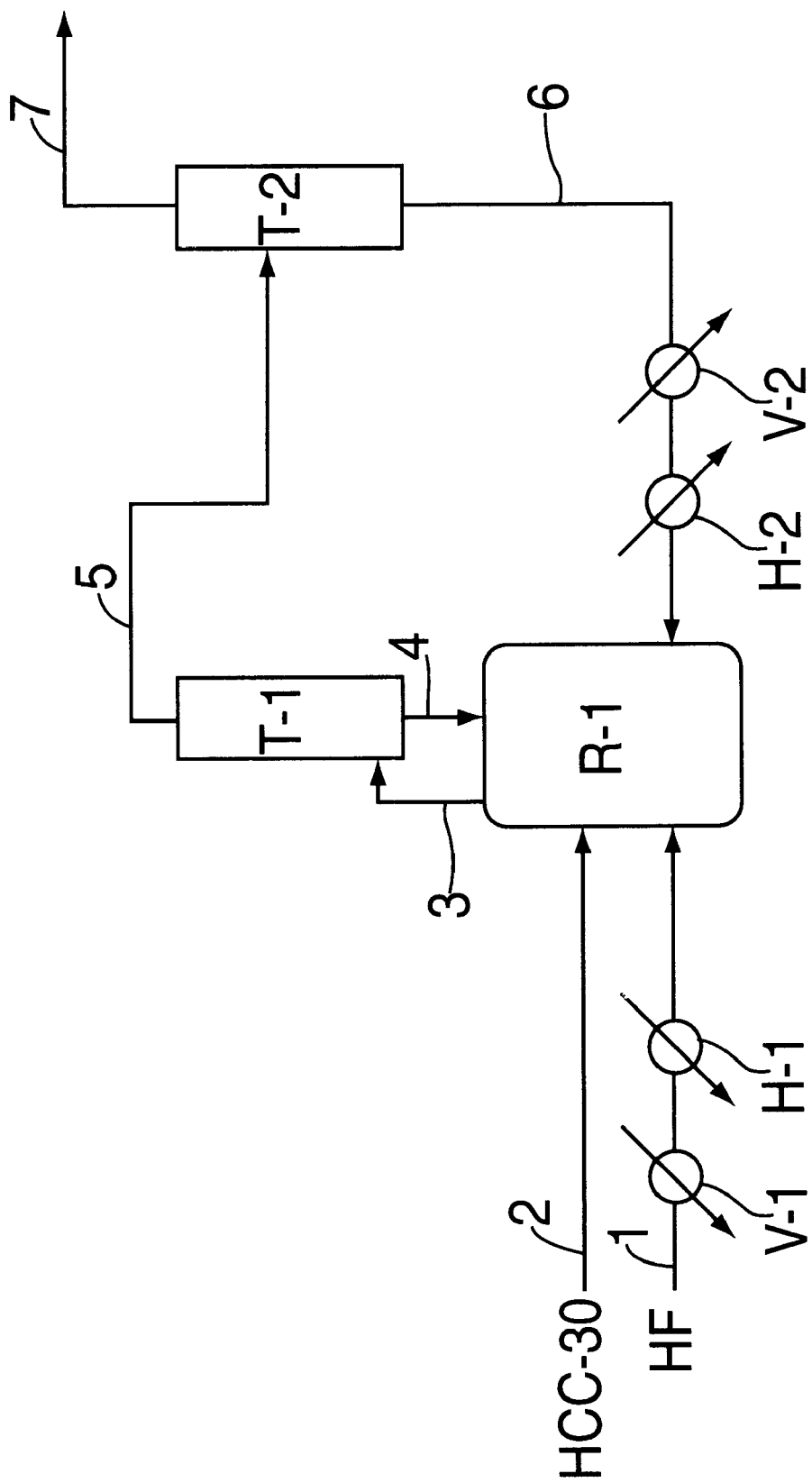
FIG. 1 is a schematic diagram illustrating one embodiment of the process of the invention.

Applicants have discovered a liquid phase fluorination process for producing HFC's without corrosion while maintaining high productivity and efficient heat transfer comprising reacting methylene chloride ("HCC-30") and hydrogen fluoride in a reactor made of fluorinated polymer and feeding concurrently a vaporized and superheated recycle stream of process reactants into the reactor.

As used herein, the terms "superheating" and "superheated" mean heating a vapor to a temperature at least about 10 to about 150° C., preferably at least about 20 to about 100° C., most preferably at least about 20 to about 50° C., above the reactor temperature. For purposes of the invention, by "process reactants" is meant at least one of hydrogen fluoride, HCC-30, monochloromonofluoromethane ("HCFC-31"), and catalyst. Also for purposes of this invention, by "made of a fluorinated polymer" means that the reactor is constructed of a fluorinated polymer, the reactor is a metal shell lined with a fluorinated polymer, or the reactor is a metal shell lined with a first layer that is a fluorinated polymer and a second layer that is made of carbon bricks or rings, such as graphite, KARBATE®, and the like. Suitable metals for the reactor metal shell may be any of the conventional materials of construction including, without limitation, carbon steel, stainless steel, INCONEL 600®, INCOLOY 825®, MONEL®, and HASTELLOY®.

Suitable fluorinated polymers useful in the reactor will be apparent to those ordinarily skilled in the art. Illustrative polymers include, without limitation, polytetrafluoroethylene polymer, perfluoroalkoxy polymer, ethylene tetrafluoroethylene polymer, vinylidene fluoride polymer, ethylene hexafluoropropylene polymer and the like. Preferably, polytetrafluoroethylene polymer is used.

The liquid phase fluorination reaction preferably takes place in the presence of an effective amount of any suitable fluorination catalyst. Suitable fluorination catalysts include, without limitation, antimony halide catalysts as well as molybdenum, titanium, tantalum, tin, niobium, and iron catalysts. The invention may find its greatest utility with antimony pentachloride catalyst. The catalyst may be treated prior to use by any known pretreatment method. The amount of catalyst used in an amount effective to catalyze the fluorination of the HCC-30. Generally the amount of catalyst is from about 1 to about 90, preferably from about 10 to about 40, weight percent of the reaction mass.

Suitable corrosion resistant equipment is used in carrying out the process of the invention. In the process, the HCC-30 and hydrogen fluoride are reacted in a reactor made of fluorinated polymer. In order to provide even more heat to the reaction, prior to being fed into the reactor fresh hydrogen fluoride is vaporized and superheated. Preferably, the fresh hydrogen fluoride is fed into the reactor through an eductor or sparger to promote mixing within the reactor. Reaction temperatures may be from about 50 to about 110° C., preferably from about 75 to about 95° C. Reaction pressures may be from about 100 to about 300 psig, preferably from about 100 to about 250 psig, and more preferably from about 100 to about 200 psig. The reactor temperature and pressure are maintained such that at least a portion of the hydrogen fluoride in the reactor is maintained in the liquid state.

Reacting the HCC-30 and hydrogen fluoride in the presence of the catalyst produces a reaction product that is a vapor mixture comprising the desired product (HFC-32), process reactants and by-product HCl. The vapor is sent to one ore more distillation columns, or other convenient apparatus, for separation. The bottom section and piping connecting the first distillation column with the reactor preferably are made of fluorinated polymer.

In all embodiments of the invention, a recycle stream of process reactants is vaporized and superheated to a temperature at least about 10 to about 150° C., preferably at least about 20 to about 100° C., above the reactor temperature. Generally, the temperature of the process reactants recycle stream fed into the reactor is between about 100 and about 200° C., preferably about 130 and about 180° C. The superheated recycle stream serves two purposes: (1) to overcome the poor heat transfer characteristics of the fluoropolymer used to make the reactor corrosion resistant by providing all or part of the heat required by the reaction (including the endothermic heat of reaction; the heat to vaporize the reaction products; and the heat to produce sufficient reflux for efficient separation in the distillation column); and (2) to enhance the rate of reaction by promoting mixing by the agitation induced when the gaseous feed is injected into the liquid reactor mass. The process of the invention substantially reduces or eliminates the need to transfer heat in the conventional method i.e. through the reactor wall, which can reduce the useful life of the reactor.

In one embodiment of the invention, fresh hydrogen fluoride, fresh HCC-30, and a recycle stream comprising mainly hydrogen fluoride, HCFC-31, and HCC-30, is fed to a reactor made of fluorinated polymer. The fresh hydrogen fluoride and the recycle stream are vaporized and superheated, together or separately. The vaporizer and super heater may be combined into a single heat exchanger. The superheated vapors are introduced into the reactor by any convenient means, preferably through a sparger, such as a perforated pipe or through an eductor to promote mixing and heat transfer into the reactor. The fresh HCC-30 preferably is not heated prior to feeding it into the reactor so as to prevent fouling of the vaporizer/superheater and to reduce by-product formation.

The reactor is connected by a pipe to a first distillation column and, through the pipe, the liquid reflux from the bottom of the column, the column bottoms, is sent back to the reactor through the same pipe or through a second pipe. The bottom section of the distillation column and piping connecting it with the reactor preferably are made of or lined with a fluorinated polymer. The distillation column is equipped with a condenser supplied with any convenient means of cooling to produce the reflux. The crude product is withdrawn from the top of the column, the column overhead, which comprises hydrogen chloride, HFC-32, HCFC-31, HCC-30, and hydrogen fluoride. This overhead stream may be fed into a second distillation column to separate the HFC-32 and hydrogen chloride as the column overhead. This overhead may then be further purified. The remaining material, comprising hydrogen fluoride, HCFC-31, and HCC-30, is withdrawn from the bottom of the second distillation column and recycled to the reactor after vaporizing at least part of this stream and superheating the vaporized portion. As stated previously, the fresh HF is also vaporized and superheated separately or together with the recycle stream. When the entire recycle and/or fresh HF stream is vaporized, the vaporization and superheating can be carried out in the same heat exchanger. The overhead product comprising HCl and HFC-32 as the main components is further purified by any means known in the art such as, for example, wet scrubbing, drying and distillation.

In another embodiment, the reactor and first distillation column are operated as in the first embodiment but the second column separates the hydrogen chloride as the second column overhead. The remaining material, hydrogen fluoride, HFC-32, HCFC-31, and HCC-30, is withdrawn as the column bottoms and fed into a third distillation column. In the third column, HFC-32 product is separated as the overhead and sent for further purification by any means known in the art such as, for example, web scrubbing, drying and distillation. The bottoms of the third column is recycled to the reactor after vaporizing at least part of this stream and superheating the vaporized portion.

In still another embodiment, the reactor is operated as in the previous embodiments but the first distillation column is operated by cooling the overhead to remove most of the HCFC-31, HF, and HCC-30 from the top product, which comprises mainly HFC-32 and HCl, and further purifying it by any means known in the art such as, for example, wet scrubbing, drying and distillation. The bottoms from the distillation is partially vaporized and the vapor is superheated before being returned to the reactor along with the portion that is not vaporized. Alternatively, the bottoms from the distillation column is returned to the reactor as a liquid, as in the previous embodiments, but a liquid sidestream is taken from an intermediate location in the distillation column. The sidestream is partially or totally vaporized and the vapor portion superheated before being returned to the reactor along with the portion that is not vaporized. This alternative has the advantage that since the sidestream contains less catalyst than the bottom stream from the distillation column, it is less corrosive and is therefore easier to handle.

The invention will be clarified further by the following non-limiting examples.

EXAMPLES

Example 1

An apparatus arranged as shown in FIG. 1 is used to produce HFC-32. Referring to FIG. 1, fresh hydrogen fluoride is vaporized in heat exchanger V-1 and superheated in super heater H-1 to about 175° C. The superheated hydrogen fluoride is fed along with liquid HCC-30, stream 2, into reactor R-1, which reactor contains antimony pentachloride catalyst and operates at a temperature of about 90° C. and a pressure of between 100–300 psig, the pressure maintained so as to keep some of the hydrogen fluoride in the reactor as a liquid.

The vapor generated from the reaction mixture, comprising hydrogen chloride, HFC-32, HCFC-31, HCC-30, hydrogen fluoride and volatilized and entrained catalyst is sent through a pipe lined with PTFE to the bottom of distillation column T-1, located above reactor R-1 and equipped with an overhead condenser to produce the liquid reflux. The heat input to the column is provided by the heat contained in the inlet streams to reactor R-1. T-1 is made of fluorinated polymer as are the trays or packing. The liquid from the bottoms of T-1, comprising all of the entrained catalyst, and a part of the HCC-30 and hydrogen fluoride, flows back to the reactor by gravity through a pipe made of a fluorinated polymer. The T-1 overhead, comprising HFC-32 and hydrogen chloride and part of the HCFC-31 along with HCC-30 and hydrogen fluoride is sent to a second distillation column T-2.

The T-2 heat input is provided by a column reboiler. In T-2, the HFC-32 and hydrogen chloride are separated in the overhead stream and sent for further processing. The T-2 bottoms, comprising HCFC-31, HCC-30, and hydrogen fluoride is sent back to reactor R-1 through vaporizer V-2 and superheater H-2. The heat input in both H-2 and V-2 is such that it supplies the heating requirements to maintain the reaction temperature and produces enough vapor and liquid traffic in T-1 to effect the desired separation in T-1. The temperature in the example is about 175° C. The process results in the production of HFC-32 with no corrosion and with increased heat transfer.

Example 2

Figure 2:
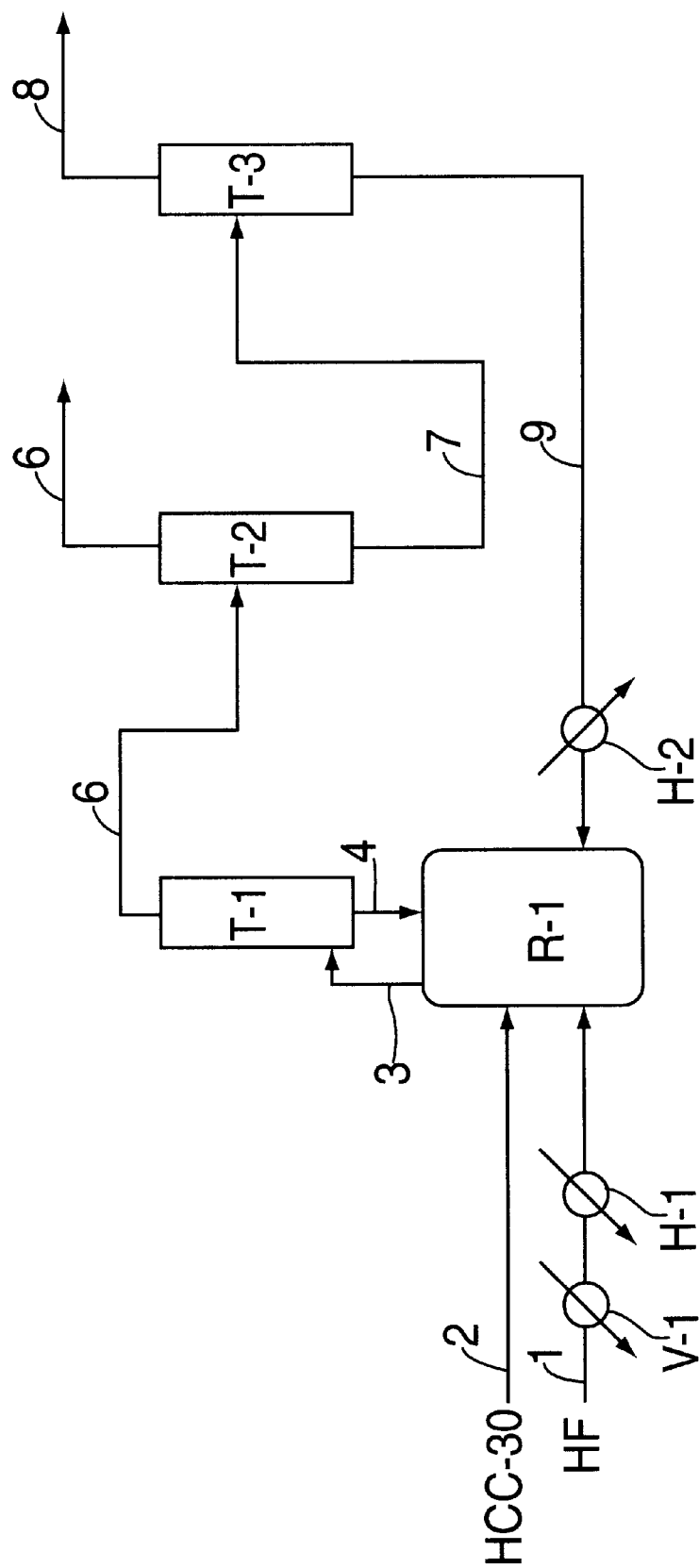
FIG. 2 is a schematic diagram illustrating another embodiment of the process of the invention.

An apparatus arranged as shown in FIG. 2 is used to produce HFC-32. Referring to FIG. 2, hydrogen fluoride is vaporized in heat exchanger V-1 and superheated in superheater H-1 to about 175° C. The superheated hydrogen fluoride is fed along with HCC-30, and into reactor R-1, which reactor contains antimony pentachloride catalyst and operates at a temperature of about 90° C. and a pressure of about 100–300 psig, so as to keep some of the hydrogen fluoride in Reactor R-1 in the liquid state.

Vapor from reactor R-1, comprising hydrogen chloride, HFC-32, HCFC-31, HCC-30, hydrogen fluoride and volatilized and entrained catalyst is sent to T-1, a first distillation column which is configured and outfitted as in Example 1. The bottoms from column T-1, comprising HCC-30 and hydrogen fluoride are sent back to reactor R-1 as in Example 1. The T-1 overhead, comprising HFC-32, hydrogen chloride, HCFC-31, HCC-30 and hydrogen fluoride is sent to a second column, T-2.

T-2 separates the hydrogen chloride as the column overhead and the bottoms stream, comprising HFC-32, HCFC- 31, HCC-30 and hydrogen fluoride is fed to a third distillation column T-3. Heat input to columns T-2 and T-3 is supplied by column reboilers. T-3 is operated at a higher pressure than reactor R-1 and separates HFC-32 in the overhead stream. The T-3 bottoms stream, comprising HCFC-31, HC-30, and hydrogen fluoride is sent to reactor R-1 through combined vaporizer and superheater H-2 at a temperature sufficient to supply the heating requirements to maintain reaction temperature and produce enough vapor in T-1 to effect the desired separation.

Example 3

Figure 3:
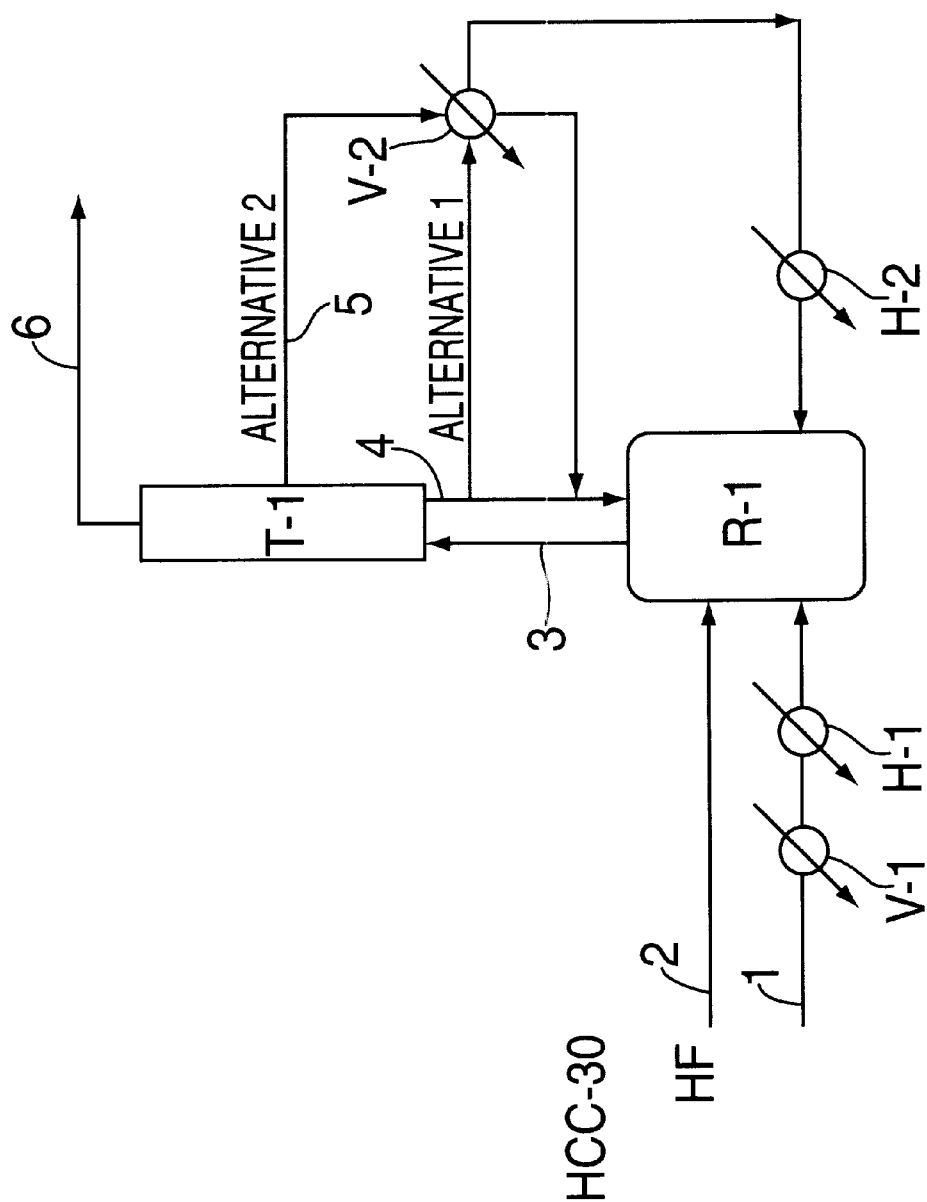
FIG. 3 is a schematic diagram illustrating yet another embodiment of the process of the invention.

An apparatus arranged as shown in FIG. 3 is used to produce HFC-32. Referring to FIG. 3, fresh hydrogen fluoride, stream 1, is vaporized in heat exchanger V-1 and superheated in superheater H-1 to about 175° C. The superheated hydrogen fluoride is fed along with liquid HCC-30, stream 2, into reactor R-1, which reactor contains antimony pentachloride catalyst and operates a temperature of about 90° C. and a pressure between 100 and 300 psig, the pressure maintained so as to keep some of the hydrogen fluoride in the reactor as a liquid. The superheated HF is preferably fed to the reactor through an eductor or sparger to promote mixing.

The vapor generated from the reaction mixture, stream 3, comprising hydrogen chloride, HFC-32, HCFC-31, HCC-30, hydrogen fluoride, and entrained and volatilized catalyst is sent through a pipe lined with PTFE to the bottom of distillation column T-1, located above reactor R-1 and equipped with an overhead condenser to produce the liquid reflux. The heat input into the column is provided by the heat contained in the inlet streams to reactor R-1. R-1 and T-1 are made or lined with a fluorinated polymer as are the trays or packing inside T-1.

In one alternative (Alternative 1) of this embodiment of the invention, the liquid from the bottom of T-1, stream 4, is partially vaporized in V-2 and the vapor from V-2 is superheated in H-2 to about 150° C. to 200° C. before it is returned to the reactor along with the liquid portion that is not vaporized in V-2. The superheated gas stream is preferably introduced into the reactor through an eductor or sparger to promote mixing.

In a second alternative (Alternative 2) of this embodiment of the invention, part of the liquid flowing down distillation column T-1 is withdrawn from an intermediate location in the column as a liquid sidestream, stream 5. In this case, the entire liquid stream can be vaporized and superheated by withdrawing the liquid sidestream from a location high enough in the column so that it does not contain any catalyst. In addition, this alternative has the added benefit that the vaporizer can be made of a metal, whereas in alternative 1, graphite based material must be used due to the corrosivity of the catalyst containing mixture. In alternative 2 the liquid from the bottom of the distillation column, stream 4, returns directly to the reactor.

The top product from the distillation column, stream 6, comprises mainly HCl and HFC-32, and the amount of HCFC-31, HCC-30, and HF in this product stream can be minimized.

What is claimed is:

1. A process comprising the steps of:
   (a) reacting reactants comprising methylene chloride and hydrogen fluoride in the presence of an effective amount of a fluorination catalyst and in a reactor made of a fluorinated polymer to produce a reaction product; and
   (b) distilling the reaction product in a first distillation column to produce a first column bottoms product that is recycled to the reactor and a first column overhead product comprising hydrogen chloride, difluoromethane, monochloromonofluoromethane, methylene chloride, and hydrogen fluoride;
   (c) distilling the first column overhead product in a second distillation column to produce a second column bottoms product comprising monochloromonofluoromethane, methylene chloride, and hydrogen fluoride and a second column overhead product comprising difluoromethane and hydrogen chloride;
   (d) vaporizing and superheating the second column bottoms product; and
   (e) recycling the vaporized and superheated second column bottoms product to the reactor.

2. The process of claim 1 wherein the first and second column bottoms products are superheated to a temperature of about 100 to about 200° C. before being recycled to the reactor.

3. A process comprising the steps of:
   (a) reacting reactants comprising methylene chloride and hydrogen fluoride in the presence of an effective amount of a fluorination catalyst and in a reactor made of a fluorinated polymer to produce a reaction product; and
   (b) distilling the reaction product in a first distillation column to produce a first column bottoms product that is recycled to the reactor and a first column overhead product comprising hydrogen chloride, difluoromethane, monochloromonofluoromethane, methylene chloride and hydrogen fluoride;
   (c) distilling the first column overhead in a second distillation column to produce a second column bottoms product comprising difluoromethane, monochloromonofluoromethane, methylene chloride, and hydrogen fluoride and a second column overhead product comprising hydrogen chloride;
   (d) distilling the second column bottoms product in a third distillation column to produce a third column bottoms product comprising monochloromonofluoromethane, methylene chloride, and hydrogen fluoride and a third column overhead product comprising difluoromethane;
   (e) vaporizing and superheating the third column bottoms product; and
   (f) recycling the vaporized and superheated third column bottoms product to the reactor.

4. The process of claim 3 wherein the first, second and third column bottoms products are superheated to a temperature of about 100 to 200° C. before being recycled to the reactor.

5. A process comprising the steps of:
   (a) reacting reactants comprising methylene chloride and hydrogen fluoride in a reactor made of a fluorinated polymer in the presence of a fluorination catalyst to produce a reaction product;
   (b) distilling the reaction product in a distillation column to produce a column bottoms product comprising hydrogen fluoride, methylene chloride and monochloromonofluoromethane and a column overhead product comprising hydrogen chloride, difluoromethane, monochloromonofluoromethane, methylene chloride, and hydrogen fluoride;
   (c) partially vaporizing the column bottoms product to produce a vapor portion and liquid portion;

(d) superheating the vapor portion; and
(e) recycling the superheated vapor portion and the liquid portion to the reactor.

6. A process comprising the steps of:
(a) reacting reactants comprising methylene chloride and hydrogen fluoride in a reactor made of a fluorinated polymer in the presence of a fluorination catalyst to produce a reaction product,
(b) distilling the reaction product in a distillation column to produce a column bottoms product comprising hydrogen fluoride, methylene chloride and monochloromonofluoromethane and a column column overhead product comprising hydrogen chloride, difluoromethane, monochloromonofluoromethane, methylene chloride, and hydrogen fluoride;
(c) withdrawing a liquid sidestream from an intermediate part of the distillation column;
(d) vaporizing and superheating the liquid sidestream; and
(e) recycling the vaporized and superheated liquid sidestream to the reactor.

7. The process of claim 6 wherein the liquid sidestream is partially vaporized to produce a vapor portion and a liquid portion; the vapor portion is superheated; and the superheated vapor portion and the liquid portion are recycled to the reactor.

* * * * *